(12) United States Patent
Carling

(10) Patent No.: US 7,785,109 B2
(45) Date of Patent: *Aug. 31, 2010

(54) MONITORING CLEANING OF SURFACES

(75) Inventor: Philip C. Carling, Hingham, MA (US)

(73) Assignee: Kleancheck Systems, LLC, Hingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/483,884

(22) Filed: Jun. 12, 2009

(65) Prior Publication Data

US 2009/0261270 A1 Oct. 22, 2009

Related U.S. Application Data

(63) Continuation of application No. 11/335,905, filed on Jan. 19, 2006, now Pat. No. 7,718,395.

(60) Provisional application No. 60/666,391, filed on Mar. 30, 2005.

(51) Int. Cl.
*G09B 23/34* (2006.01)
*C12N 1/20* (2006.01)
*C12N 1/00* (2006.01)
*G06Q 10/00* (2006.01)
*G06Q 50/00* (2006.01)
*G01N 21/00* (2006.01)
*B60R 11/00* (2006.01)

(52) U.S. Cl. .............. 434/370; 434/365; 435/252.1; 435/252.4; 435/252.7; 435/842; 435/882; 435/967; 705/11; 250/459.1; 296/24.34; 296/37.8; 296/1.09; 297/188.16

(58) Field of Classification Search ............... 434/365, 434/370; 435/252.1, 252.4, 252.7, 842, 882, 435/967; 705/11; 250/459.1; 296/24.34, 296/37.8, 1.09; 297/188.16

See application file for complete search history.

(56) References Cited

U.S. PATENT DOCUMENTS

| | | | |
|---|---|---|---|
| 2,600,221 A | 6/1952 | Domingo | 250/71 |
| 3,309,274 A | 3/1967 | Brilliant | 167/84.5 |
| 3,640,889 A | 2/1972 | Stewart | 252/301.2 R |
| 3,716,488 A | 2/1973 | Kolsky et al. | 252/155 |
| 5,084,327 A | 1/1992 | Stengel | 428/206 |
| 5,108,643 A | 4/1992 | Loth et al. | 252/174.11 |
| 5,116,533 A | 5/1992 | Grandmont et al. | 252/301.36 |
| 5,203,638 A | 4/1993 | Redmond, Jr. | 401/17 |
| 5,453,120 A | 9/1995 | Rendino et al. | 106/19 B |
| 5,498,280 A | 3/1996 | Fistner et al. | 106/19 B |
| 5,900,067 A | 5/1999 | Jones | 134/1 |
| 6,476,385 B1 | 11/2002 | Albert | 250/302 |
| 6,524,390 B1 | 2/2003 | Jones | 134/1 |
| 6,943,348 B1 | 9/2005 | Coffin, IV | 250/302 |
| 6,949,205 B2 | 9/2005 | Pendergrass | 252/301.36 |
| 2002/0192755 A1 | 12/2002 | Francis et al. | 435/69.1 |
| 2003/0197122 A1 | 10/2003 | Faiola et al. | 250/302 |
| 2005/0203213 A1 | 9/2005 | Pommiers et al. | 523/210 |
| 2006/0223731 A1* | 10/2006 | Carling | 510/156 |
| 2009/0042757 A1 | 2/2009 | Carling | 510/100 |
| 2009/0248499 A1* | 10/2009 | Carling | 250/459.1 |

OTHER PUBLICATIONS

Ansari et al., Rotavirus Survival on Human Hands and Transfer of Infectious Virus to Animate and Nonporous Inanimate Surfaces:, *J. Clin. Micro.*, vol. 26, No. 8, pp. 1513-1518 (1988).

Apisarnthanarak et al., "Effectiveness of Environmental and Infection Control Programs to Reduce Transmission of *Clostridium difficile*", *Clin. Infect. Dis.*, vol. 39, pp. 601-602 (2004).

Bhalla et al., "Acquisition of Nosocomial Pathogens on Hands After Contact With Environmental Surfaces Near Hospitalized Patients", *Infect. Control Hosp. Epidemiol.*, vol. 25, pp. 164-167 (2004).

Bonten et al., "Epidemiology of colonisation of patients and environment with vancomycin-resistant enterococci", *The Lancet*, vol. 348, pp. 1615-1619 (1996).

Boyce et al., "Do Infection Control Measures Work for Methicillin-Resistant *Staphyloococcus aureus?*", *Infect. Control Hosp. Epidemiol.*, vol. 25, No. 5, 395-401 (2004).

Boyce et al., "Environmental Contamination Due to Methicillin-Resistant *Staphylococcus aureus*: Possible Infection Control Implications", *Infect. Control Hosp. Epidemiol.*, vol. 18, No. 9, pp. 622-627 (1997).

Boyce et al., Controlling Vancomycin-Resistant Enterococci, *Infect. Control Hosp. Epidemiol.*, vol. 16, No. 11, pp. 634-637 (1995).

Boyce et al., "Outbreak of Multidrug-Resistant *Enterococcus faecium* with Transferable *vanB* Class Vancomycin Resistance", *J. Clin. Micro.*, vol. 32, No. 5, pp. 1148-1153 (1994).

Bures et al., "Computer keyboards and faucet handles as reservoirs of nosocomial pathogens in the intensive care unit", *Am. J. Infect. Control*, vol. 28, No. 6, pp. 465-471 (2000).

Byers et al., "Disinfection of Hospital Rooms Contaminated with Vancomycin-Resistant *Enterococcus faecium*", *Infect. Control Hosp. Epidemio.*, vol. 19, No. 4, pp. 261-264 (1998).

Carling et al., "A Prospective Evaluation of Patient Room Cleaning in Two Hospitals Using a Novel Targeting Methodology", Society for Healthcare Epidemiology of America (Abstract Control No. 04-A-127-SHEA—2 pages) (2004).

Carling et al., "A Prospective Evaluation of Patient Room Cleaning in Two Hospitals Using a Novel Targeting Methodology", The Fourteenth Annual Scientific Meeting of the Society for Healthcare Epidemiology of America, No. 237, p. 103 (2004).

(Continued)

*Primary Examiner*—Jon P Weber
*Assistant Examiner*—Kailash C Srivastava
(74) *Attorney, Agent, or Firm*—Sunstein Kann Murphy & Timbers LLP

(57) ABSTRACT

A method for monitoring cleaning of a surface includes applying an amount of transparent indicator material to an area of a surface and measuring the amount of transparent indicator material remaining on the surface. The transparent indicator material may be fixed on the surface by drying and, when a fluorescent material, may be measured through exposure to ultraviolet radiation.

49 Claims, 14 Drawing Sheets

OTHER PUBLICATIONS

Carling et al., "An Evaluation of Patient Room Cleaning in Three Intensive Care Units Using a Novel Targeting Methodology", Abstracts of the 44th Interscience Conference on Antimicrobial Agents and Chemotherapy (ICAAC), Session 163(K), Washington, D.C., p. 376 (Abstract Only—K-1601) (2004).

Centers for Disease Control and Prevention, "Recommendations for Preventing the Spread of Vancomycin Resistance: Recommendations of the Hospital Infection Control Practices Advisory Committee (HICPAC)", Available at: http://wonder.cdc.gov/wonder/prevguid/m0039349/m0039349.asp, MMWR, 14 pages (1995).

Christiansen et al., "Eradication of a Large Outbreak of A Single Strain of vanB Vancomycin-Resistant *Enterococcus faecium* At A Major Australian Teaching Hospital", *Infect. Control Hosp. Epidemiol.*, vol. 25, pp. 384-390 (2000).

Clarke et al., "Persistence of vancomycin-resistant enterococci (VRE) and other bacteria in the environment", *Ir Med. J.*, vol. 94, No. 9, 6 pages (2001).

Davidson et al., "Evaluation of two methods for monitoring surface cleanliness—ATP bioluminescence and traditional hygiene swabbing", *Luminescence*, vol. 14, pp. 33-38 (1999).

Department of Health, "Winning Ways—Working together to reduce healthcare associated infection in England", Report from the Chief Medical Officer, London, England, 28 pages Available at: www.dh.gov.uk/en/Publicationsandstatistics/Publications (Accessed Dec. 2003).

Department of Health and Human Services, "Draft Guideline for Isolation Precautions: Preventing Transmission of Infectious Agents in Healthcare Settings", Centers for Disease Control and Prevention, *Fed. Reg.*, vol. 69, No. 113, p. 33034 (2004).

Diekema et al., "Antimicrobial Resistance Trends and Outbreak Frequency in United States Hospitals", *Clin. Infect. Dis.*, vol. 38, pp. 78-85 (2004).

Diekema, "Use of Active Surveillance Cultures to Control Vancomycin-Resistant *Enterococcus*", *Clin. Infect. Dis.*, vol. 37, pp. 1400-1403 (2003).

Dominguez et al., "Spread and Maintenance of a Dominant Methicillin-Resistant *Staphylococcus aureus* (MRSA) Clone During an Outbreak of MRSA Disease in a Spanish Hospital", *J. Clin. Micro.*, vol. 32, No. 9, pp. 2081-2087 (1994).

Donskey et al., "Effect of Antibiotic Therapy on the Density of Vancomycin-Resistant Enterococci in the Stool of Colonized Patients", *N. Eng. J. Med.*, vol. 343, No. 26, pp. 1925-1932 (2000).

Donskey, "The Role of the Intestinal Tract as a Reservoir and Source for Transmission of Nosocomial Pathogens", *Clin. Infect. Dis.*, vol. 39, pp. 219-226 (2004).

Edmond et al., "Vancomycin-Resistant *Enterococcus faecium* Bacteremia: Risk Factors for Infection", *Clin. Infect. Dis.*, vol. 20, pp. 1126-1133 (1995).

Falk et al., "Outbreak of Vancomycin-Resistant Enterococci In A Burn Unit", *Infect. Control Hosp. Epidemiol.*, vol. 21, No. 9, pp. 575-582 (2000).

Farr et al., "Can antibiotic-resistant nosocomial infections be controlled?", *The Lancet Infect. Dis.*, vol. 1, pp. 38-45 (2001).

Farr, "For Nosocomial Vancomycin-Resistant Enterococcal Infections: The Ounce of Prevention or the Pound of Cure?", *Clin. Infect. Dis.*, vol. 38, pp. 1116-1118 (2004).

Fekety et al., "Epidemiology of Antibiotic-Associated Colitis: Isolation of Clostridium Difficile from the Hospital Environment", *Am. J. Med.*, vol. 70, pp. 906-908 (1981).

French et al., "Survival of Nosocomial Bacteria Dried in Air and Killing by Hydrogen Peroxide Vapour (HPV)", Abstracts of the 44th Interscience Conference on Antimicrobial Agents and Chemotherapy (ICAAC), Session 163(K), Washington, D.C., p. 376 (Abstract Only—K-1602) (2004).

French et al., "Tackling contamination of the hospital environment by methicillin resistant *Staphylococcus aureus* (MRSA): a comparison between conventional terminal cleaning and hydrogen peroxide vapour decontamination", *J. Hosp. Infect.*, vol. 57, No. 1, pp. 31-37 (2004).

Gerberding, "Hospital-Onset Infections: A Patient Safety Issue", *Ann. Intern. Med.*, American College of Physicians—American Society of Internal Medicine, vol. 137, No. 8, pp. 665-670 (2002).

Gould et al., "Nosocomial infection with microsphere beds", *The Lancet*, vol. 342, pp. 241-242 (1993).

Griffith et al., "Environmental surface cleanliness and the potential for contamination during handwashing", *Am. J. Infect. Control*, vol. 31, No. 2, pp. 93-96 (2003).

Griffith et al., "An evaluation of hospital cleaning regimes and standards", *J. Hosp. Infect.*, vol. 45, pp. 19-28 (2000).

Hoffman et al., "Environmental Management Services Project Enhances Infection Control Program", Abstracts of the Association for Practitioners in Infection Control Educational Conference and International Meeting, Phoenix, Arizona (Abstract ID No. 22353—1 page) (2004).

Hota, "Contamination, Disinfection, and Cross-Colonization: Are Hospital Surfaces Reservoirs for Nosocomial Infection?", *Clin. Infect. Dis.*, vol. 39, pp. 1182-1189 (2004).

Infectious Diseases Society of America, "Bad Bugs, No Drugs", Available at: http://www.idsociety.org, 37 pages (2004).

Jackson et al., "HICPAC/SHEA—Conflicting guidelines: What is the standard of care?", *Am. J. Infect. Control*, vol. 32, No. 8, pp. 504-511 (2004).

Kaatz et al., "Acquisition of *Clostridium difficile* from the Hospital Environment", *Am. J. Epid.*, vol. 127, No. 6, pp. 1289-1294 (1988).

Kampf et al., "Epidemiologic Background of Hand Hygiene and Evaluation of the Most Important Agents for Scrubs and Rubs", *Clin. Microbiol. Rev.*, vol. 17, No. 4, pp. 863-893 (2004).

Kim et al., "Rates of hand disinfection associated with glove use, patient isolation, and changes between exposure to various body sites", *Am. J. Infect. Control*, vol. 31, No. 2, pp. 97-103 (2003).

Kim et al. "Isolation of *Clostridium difficile* from the Environment and Contacts of Patients with Antibiotic-Associated Colitis", *J. Infect. Dis.*, vol. 143, No. 1, pp. 42-50 (1981).

Lai et al., "Failure to Eradicate Vancomycin-Resistant Enterococci in a University Hospital and the Cost of Barrier Precautions", *Infec. Control Hosp. Epidemiol.*, vol. 19, pp. 647-652 (1998).

Layton et al., "An Outbreak of Mupirocin-Resistant *Staphylococcus aureus* on a Dermatology Ward Associated With an Environmental Reservoir", *Infect. Control Hosp. Epidemiol.*, vol. 14, No. 7, pp. 369-375 (1993).

Lemmen et al. "Distribution of multi-resistant Gram-negative versus Gram-positive bacteria in the hospital inanimate environment", *J. Hosp. Infect.*, vol. 56, pp. 191-197 (2004).

Linkin et al., "Risk Factors for Extended-Spectrum Beta-Lactamase-Producing Enterobacteriaceae in a Neonatal Intensive Care Unit", *Infect. Control Hosp. Epidemiol.*, vol. 25, No. 9, pp. 781-783 (2004).

Livornese et al., "Hospital-acquired Infection with Vancomycin-resistant *Enterococcus faecium* Transmitted by Electronic Thermometers", *Ann. Intern. Med.*, vol. 117, No. 2, pp. 112-116 (1992).

Malik et al., "Use of audit tools to evaluate the efficacy of cleaning systems in hospitals", *Am. J. Infect. Control*, vol. 31, No. 3, pp. 181-187 (2003).

Mayer et al., "Role of fecal incontinence in contamination of the environment with vancomycin-resistant *enterococci*", *Am. J. Infect. Control*, vol. 31, No. 4 (Abstract Only—2 pages) (2003).

Mayfield et al., "Environmental Control to Reduce Transmission of *Clostridium difficile*", *Clin. Infect. Dis.*, vol. 31, pp. 995-1000 (2000).

McFarland et al., "Nosocomial Acquisition of *Clostridium difficile* Infection", *N. Eng. J. Med.*, vol. 320, No. 4, pp. 204-210 (1989).

Muto et al., "SHEA Guideline for Preventing Nosocomial Transmission of Multidrug-Resistant Strains of *Staphylococcus aureus* and *Enterococcus*", *Infect. Control Hosp. Epidemiol.*, vol. 24, No. 5, pp. 362-386 (2003).

Nath et al., "A Sustained Outbreak of *Clostridium difficile* In A General Hospital: Persistence of A Toxigenic Clone in Four Units", *Infect. Control Hosp. Epidemiol.*, vol. 15, pp. 382-389 (1994).

Nijssen et al., "Are Active Microbiological Surveillance and Subsequent Isolation Needed to Prevent the Spread of Methicillin-Resistant *Staphylococcus aureus*?", *Clin. Infect. Dis.*, Surveillance, Isolation, and Spread of MRSA, vol. 40, pp. 405-409 (2005).

Noskin et al., "Engineering Infection Control through Facility Design", *Emerg. Infect. Dis.*, Special Issue, vol. 7, No. 2, pp. 354-356 (2001).

Oie et al., "Contamination of room door handles by methicillin-sensitive/methicillin-resistant *Staphylococcus aureus*", *J. Hosp. Infect.*, vol. 51, pp. 140-143 (2002).

Pyrek, "Infection Prevention—Through Proper Hand Hygiene and Gloving", *Infect. Control Today*, Available at http://www.infectioncontroltoday.com/articles/4a1feat1.html, 4 pages (2005).

Rampling et al., "Evidence that hospital hygiene is important in the control of methicillin-resistant *Staphylococcus aureus*", *J. Hosp. Infect.*, vol. 49, pp. 109-116 (2001).

Ray et al., "Nosocomial Transmission of Vancomycin-Resistant Enterococci From Surfaces", JAMA, vol. 287, No. 111, pp. 1400-1401 (2002).

Rutala et al., "New Disinfection and Sterilization Methods", *Emerg. Infect. Dis.*, Special Issue, vol. 7, No. 2, pp. 348-353 (2001).

Rutala et al., "Surface disinfection: should we do it?", *J. Hosp. Infect.*, vol. 48 (Supp.) pp. S64-S68 (2001).

Rutala et al., "Infection control: the role of disinfection and sterilization", *J. Hosp. Inf.*, vol. 43 (Supp.), pp. S43-S55 (1999).

Rutala et al., "Susceptibility of Antibiotic-Susceptible and Antibiotic-Resistant Hospital Bacteria to Disinfectants", *Infect. Control Hosp. Epidemiol.*, vol. 18, No. 6, pp. 417-421 (1997).

Rutala et al., Environmental Study of a Methicillin-Resistant *Staphylococcus aureus* Epidemic in a Burn Unit, *J. Clin. Micro.*, vol. 18, No. 3, pp. 683-688 (1983).

Rutala, "APIC Guideline for Selection and Use of Disinfectants", *Am. J. Infect. Control*, APIC Guidelines for Infection Control Practice (Supp.), vol. 24, No. 4, pp. 313-342 (1996).

Samore et al., "Clinical and Molecular Epidemiology of Sporadic and Clustered Cases of Nosocomial *Clostridium difficile* Diarrhea", *Am. J. Med.*, vol. 100, pp. 32-40 (1996).

Sehulster et al., "Guidelines for Environmental Infection Control in Healthcare Facilities: Recommendations of CDC and the Healthcare Infection Control Practices Advisor Committee (HICPAC)", Centers for Disease Control and Prevention, Atlanta, Georgia, Available at www.cdc.gov, pp. 1-63 (Accessed Dec. 2004).

Shay et al., "Epidemiology and Mortality Risk of Voncomycin-Resistant Enterococcal Bloodstream Infections", *J. Infect. Dis.*, vol. 172, pp. 993-1000 (1995).

Sheretz et al., "A Cloud Adult: The *Staphylococcus aureus*—Virus Interaction Revisited", *Ann. Intern. Med.*, vol. 124, No. 6, pp. 539-547 (1996).

Slaughter et al., "A Comparison of the Effect of Universal Use of Gloves and Gowns with That of Glove Use Alone on Acquisition of Vancomycin-Resistant Enterococci in a Medical Intensive Care Unit", *Ann. Intern. Med.*, vol. 125, No. 6, pp. 448-456 (1996).

Stiefel et al., "Increased Susceptibility to Vancomycin-Resistant *Enterococcus* Intestinal Colonization Persists After Completion of Anti-Anaerobic Antibiotic Treatment in Mice", *Infect. Control Hosp. Epidemio.*, vol. 25, No. 5, pp. 373-379 (2004).

Smith et al., "Environmental Contamination With Vancomycin-Resistant Enterococci in an Outpatient Setting", *Infect. Control Hosp. Epidemiol.*, vol. 19, No. 7, pp. 515-518 (1998).

Srinivasan et al., "A Prospective Study to Determine Whether Cover Gowns in Addition to Gloves Decrease Nosocomial Transmission of Vancomycin-Resistant Enterococci in an Intensive Care Unit", *Infect. Control Hosp. Epidemiol.*, vol. 23, No. 8, pp. 424-428 (2002).

Struelens et al., "Control of Nosocomial Transmission of *Clostridium difficile* Based on Sporadic Case Surveillance", *Am. J. Med.*, vol. 91 (Supp. 3B), pp. 138S-143S (1991).

Tiemersma et al., "Methicillin-resistant *Staphylococcus aureus* in Europe, 1999-2002", *Emerg. Infect. Dis.*, vol. 10, pp. 1627-1634 (2004).

Van et al., "Environmental Contamination in Child Day-Care Centers", *Am. J. Epidemiol.*, vol. 133, No. 5, pp. 460-470 (1991).

Weber et al., "Role of Environmental Contamination in the Transmission of Vancomycin-Resistant Enterococci", *Infect. Control Hosp. Epidemiol.*, vol. 18, No. 5, pp. 306-309 (1997).

Weinstein, "Controlling Antimicrobial Resistance in Hospitals: Infection Control and Use of Antibiotics", *Emerg. Infec. Dis.*, Special Issue, vol. 7, No. 2, pp. 188-192 (2001).

Widmer et al., "Alcohol-based Handrub: Evaluation of Technique and Microbiological Efficacy With International Infection Control Professionals", *Infect. Control Hosp. Epidemiol*, vol. 25, No. 3, pp. 207-209 (2004).

Wullt et al., "Activity of Three Disinfectants and Acidified Nitrite Against *Clostridium difficile* Spores", *Infect. Control Hosp. Epidemiol.*, vol. 24, No. 10, pp. 765-768 (2003).

* cited by examiner

Contaminated Surfaces

| | VRE | MRSA | C. Difficile |
|---|---|---|---|
| Bed Rails | +++++++ | + | +++ |
| Bed Table | ++++++ | + | |
| Door Knobs | ++ | ++ | + |
| Doors | +++ | + | |
| Call Button | +++ | + | ++ |
| Chair | ++ | + | ++ |
| Tray Table | +++ | ++ | |
| Toilet Surface | + | | ++++ |
| Sink Surface | + | + | +++ |
| Bedpan Cleaner | | | + |

FIG. 1

Survival of Pathogens on
Environmental Surfaces

C. Difficile - > 5 months
MRSA - 90 to > 236 d.
VRE - 7 to 120 d.
E. coli O 157 - > 60 d.

Rhinoviruses - Several Hours
Hepatitis A - > 4 hours
Parainfluenza viruses - 10 hours Target After Marking

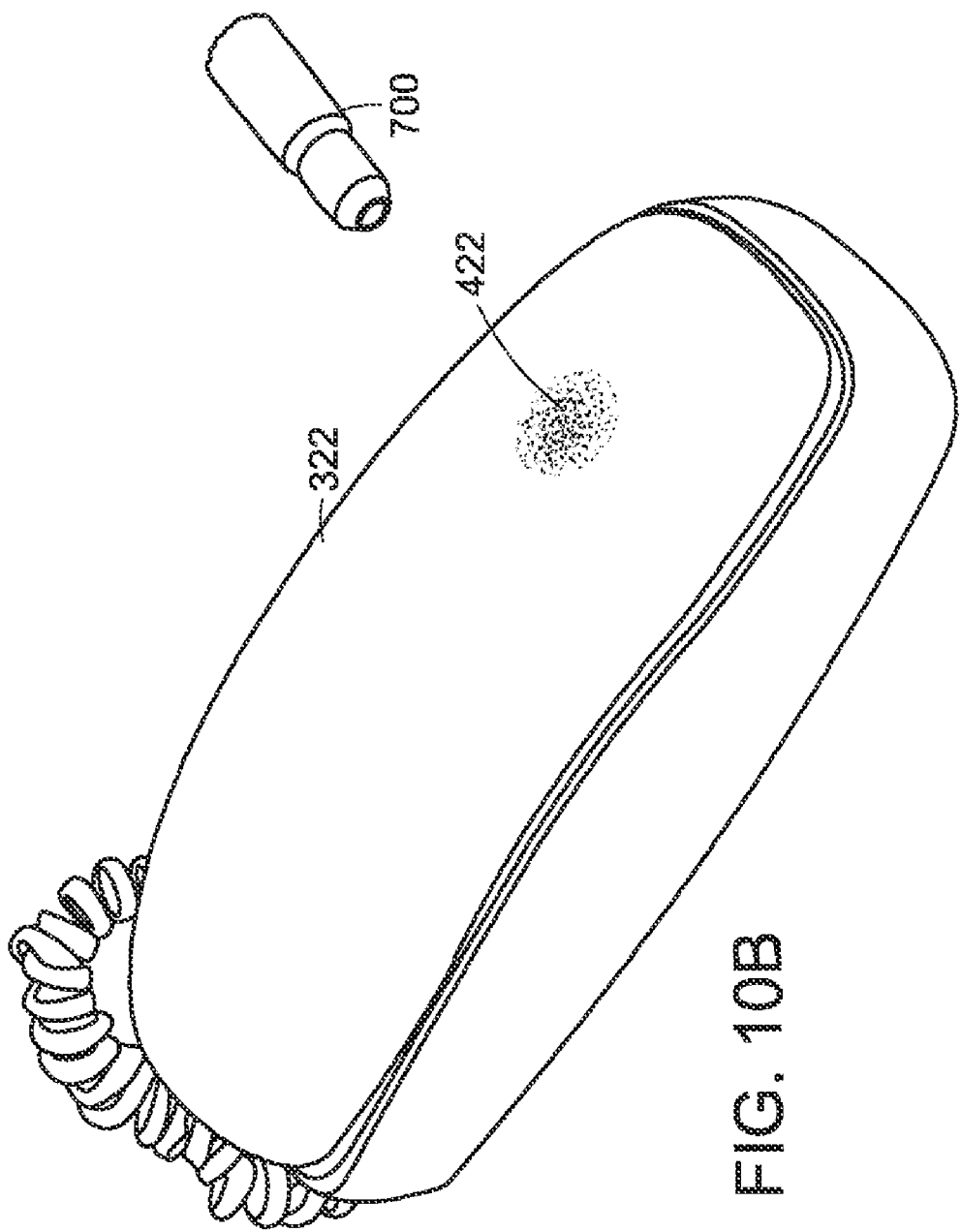

EnviroCheck Systems

Level I Participant Program

⟋ 1100

1120 → Environmental Evaluation          (Phase 1)

A. Introduction training. ( ICP - 1.5 hr.)
        EnviroCheck Systems overview
        Role of near patient environment in infection prevention
        Evaluation technology B. Pre-intervention data collection ( ICP - 3.0 hr. over 4 weeks)

C. Intra-institutional comparison and evaluation.

D. Programmatic support.-Ongoing

1140 → Program Enhancement          (Phase II)

A. Administrative leadership[1] education related to Phase I and agreement to develop a Quality Improvement action plan.

B. Completion of Participant Agreement

C. Site specific Demographic Data Set collection ( ICP - 1.0 hr.)

D. Senior hospital administration[2] educational intervention related to Phase I ( ICP - 1.0 hr.)

E. Environmental services staff[3] educational intervention related to Phase I* ( B - D above ) ( ICP 2.0 hr.)

F. Implementation of targeted Cleaning and Disinfect ion Program. ( ICP - 1.0 hr.)

G. Evaluation of initial intervention program.[4] ( ICP - 2.0 hr. over 4 weeks )

FIG. 15A

H. Administrative and Environmental Service Feedback of pre/post intervention results, including :

1. General administration presentation. (ICP - 1.0 hr.)

2. Graphic feedback to environmental services. (Excel templates provided) (ICP - 1.0 hr.)

3. Graphic feedback to nursing units. (Excel templates provided) (ICP - 1.0 hr)

I. Further programmatic evaluation - (ICP - 2.0 over 4 wk.)

J. Programmatic feedback (as in H above) (ICP - 1.0 hr.)

K. Assistance with JCAHO Presentation

1160 → PROGRAM COMPARISION (Phase III)

A. Programmatic evaluation - ongoing (ICP 2.0 hr. each 6 months)

B. Programmatic feedback (as in H above) (ICP 1.0 - hr. each 6 months)

C. Inter-Institutional comparison - ongoing (1.0 hr. every months)

D. Administrative feedback ongoing through Infection Control Committee.

E. Programmatic and individual recognition.

F. Consideration of other applications.

FOOTNOTES

1. Directors of Quality Assurance, Patient Care and usually the Director of Environmental Services, although it may be better for the ICP to educate and enlist the support of the latter individual separately.

2. The Senior Hospital Leadership Group Group which goes by different terms at different hospital.

3. To include all supervisor and personnel from all shifts.

4. Done three to four weeks after program implementation complete.
  * Power Point program template provided

FIG. 15B

MONITORING CLEANING OF SURFACES

PRIORITY

This patent application is a continuation of and claims priority from all priority dates of U.S. patent application Ser. No. 11/335,905, filed Jan. 19, 2006, and entitled "Monitoring Cleaning of Surfaces". As a consequence of this priority claim, this patent application also claims priority to the U.S. Provisional Patent Application 60/666,391, filed Mar. 30, 2005, and entitled "Monitoring Cleaning of Surfaces." The disclosures of each of these applications are incorporated herein by reference in their entirety.

RELATED UNITED STATES PATENT APPLICATIONS

This patent application is related to the following co-pending U.S. patent applications:

U.S. patent application Ser. No. 12/255,304, entitled, "Monitoring Cleaning of Surfaces," naming Philip C. Carling as inventor, filed on Oct. 21, 2008, the disclosure of which is incorporated herein, in its entirety, by reference.

U.S. patent application Ser. No. 12/483,872, entitled, "Monitoring Cleaning of Surfaces," naming Philip C. Carling as inventor, filed on even date herewith, the disclosure of which is incorporated herein, in its entirety, by reference.

TECHNICAL FIELD

The present invention relates to monitoring cleaning of surfaces, and, more particularly, to monitoring cleaning of surfaces in health care environments.

BACKGROUND

Although environmental cleaning and disinfecting practices have become a cornerstone of patient care, assessment of actual compliance with such procedures has not been reported. During the past decade controlling and limiting the spread of health care associated pathogens has become one of the most challenging and aspects of health care epidemiology. Unfortunately the continuing escalation of infections with these pathogens has led to more than 1.5 million people developing resistant hospital acquired, i.e., nosocomial, infections in the U.S. annually. Despite enhancement of hand hygiene through the development of user friendly alcohol based hand cleansers, the manner in which they are used and the difficulty achieving appropriate compliance with their use potentially limit their effectiveness.

Three pathogens posing significant nosocomial problems are MRSA (Methicillin Resistant *Staphylococcus aureus*), VRE (Vancomycin Resistant *Enterococcus*), and *Clostridium difficile* (*C. difficile*). Their importance derives from a combination of resistance to presently available treatments and an ability to rapidly spread extensively in the environment around hospitalized patients. MRSA is present in wound infections, as associated with bed sores and catheters. VRE is present in bowel and urinary tract infections. *C. difficile* is also present in bowel infections and presents as severe diarrhea. For each of these pathogens, control with present antibiotics is problematical, if not impossible.

Although screening based isolation practices have been advocated to limit the transmission of MRSA and VRE, there are logistical issues and concerns about the practical application and cost effectiveness of such practices. Reliance on such practices may alter the epidemiology but not the incidence of health care associated infections. Additionally, outbreak persistence as well as significant environmental contamination occurs despite patients being on isolation for VRE and MRSA as well as for patients who are asymptomatically colonized with *C. difficile* for which screening is not feasible. These programmatic as well as pathogen based issues clearly have limited the effectiveness of current as well as proposed isolation practices.

Enhancement of existing cleaning and disinfection practices deserves further consideration and evaluation. Although it is not currently feasible to define the independent role of the hospital environment in the transmission of health care associated pathogens except in isolated investigations, numerous studies over the past twenty years have confirmed the frequent contamination (FIG. 1) of many surfaces in the near patient environment (FIG. 2) with hospital associated pathogens able to survive on inanimate surfaces for weeks to months (FIG. 3).

With respect to individual pathogens, it has been found that high rates of environmental contamination with *C. difficile* have been associated both with symptomatic as well as asymptomatic patients. Direct evaluation of the role of environmental contamination in the transmission of *C. difficile* found a strong correlation with the intensity of environmental contamination, and outbreaks of *C. difficile* infection have been successfully terminated by enhanced cleaning/disinfecting activities.

The role of environmental contamination in transmission of VRE has been documented. Recent studies have confirmed the frequency of environmental contamination, shown to be highly correlated with the number of body sites colonized as well as with the intensity of gastrointestinal tract colonization. Furthermore the ease with which gloved hands can become contaminated by limited contact with a colonized patient's bed rail and bedside table the rapid recontamination of surfaces in the near patient environment with VRE despite effective daily cleaning even in the absence of diarrhea as well as the termination of a VRE outbreak in an ICU through enhanced cleaning activities support the likely importance of the environment in the epidemiology of VRE.

MRSA is frequently found in the environment of both colonized and infected patients and colonized health care workers. The pathogen can be transmitted by the gloves of health care providers and increases in concentration in the stool of colonized patients receiving broad spectrum antibiotics. Consequently, it is likely that environmental contamination plays a role in the spread of MRSA. In addition, DNA typing in three studies has supported the likely importance of environmental reservoirs in colonal MRSA outbreaks in hospitals lasting from three months to five years.

These and similar observations confirm the longstanding belief that environmental cleaning/disinfecting activities are important in providing an optimally safe environment for patients and have led to the development of specific guidelines for environmental infection control in health care facilities. Environmental disinfecting does work. Materials such as phenolic compounds, quartinary ammonium compounds, chloride disinfectants, and formaldehyde can kill a wide range of microbial pathogens, work rapidly, and work effectively in clinical settings as shown in FIG. 4.

In 2002, the Centers of Disease Control (CDC) recommended that hospitals "thoroughly clean and disinfect environmental medical equipment surfaces on a regular basis". Similarly, the Society for Health Care Epidemiology of America's position paper regarding enhanced interventions to control the spread of resistant *Staphylococcus aureus* and *Enterococcus* recommended that hospitals "ensure" that their institutional methods of disinfecting surfaces be shown to be "adequate". In 2003, the National Health Service of Great Britain specifically recommended that "cleaning and disinfecting programmes and protocols for environmental surfaces in patient care areas should be defined".

Most recently the draft guidelines for isolation precautions developed by the CDC in 2004 emphasize the importance of environmental cleaning and disinfection activities. Draft guidelines for isolation precautions developed by the CDC emphasize the importance of environmental cleaning and disinfection activities. Although these guidelines specifically state that hospitals "ensure compliance by housekeeping staff with cleaning and disinfecting procedures" and "insure consistent cleaning and disinfection of surfaces in close proximity to the patient and likely to be touched by the patient and health care worker", they provide no directives regarding the means by which hospitals are to assist their ability to comply with or "insure" the effectiveness of such activities prospectively.

In a similar manner the Joint Commission for Health Care Accreditation 2004 standard states "hospitals are expected to develop standards to measure staff and hospital performance in managing and improving the environment of care" without defining what specific resources should be utilized to carry out such activities.

In view of the above, there is a need for a non-microbiological methodology to evaluate the thoroughness with which housekeeping activities are carried out in hospitals.

SUMMARY OF THE INVENTION

In accordance with one aspect of the invention, a method for monitoring cleaning of a surface includes applying an amount of transparent indicator material to an area of a surface and measuring the amount remaining on the surface. The transparent indicator material may be fixed to the area of the surface, as by drying. The transparent indicator material may be a fluorescent material and measuring the amount of remaining on the surface may include exposing the area to ultraviolet radiation.

Some embodiments may include one or more opportunities for reducing the amount of the transparent indicator material whose location may be unknown to the receiver of the opportunity. Reducing the amount may be a part of cleaning the surface. The opportunity to reduce the amount of transparent indicator material may be suspended at the expiration of a period of time following initiation, where the period may be a day or less, between a day and a week, or between a week and a month.

In accordance with another aspect of the invention, a composition for monitoring cleaning of a surface includes a carrier, a transparent indicator soluble in the carrier, a transparent source of adherence to the surface soluble in the carrier, and a surfactant. In certain embodiments, the carrier may be soluble in water and the carrier may be a detergent. In other embodiments the transparent indicator may be fluorescent under ultraviolet radiation. In additional embodiments, the transparent source of adherence may be a natural glue such as methyl cellulose.

In accordance with a further aspect of the invention, a method for control of nosocomial pathogens includes evaluating a cleaning program for a patient-care environment within a facility, enhancing the cleaning program for the patient care environment, and comparing the enhanced cleaning program with at least one other cleaning program. In certain embodiments, evaluating a cleaning program may include training with monitoring surfaces, collecting pre-intervention data, and comparing control within the facility.

In other embodiments, enhancing the cleaning program may include collecting site-specific demographic data, providing education to administrative leadership, senior hospital administration and environmental services staff, implementing a targeted cleaning and disinfection program, evaluating an initial intervention program, obtaining feedback of pre and post intervention results, and assisting with a presentation to the Joint Commission on Accreditation of Healthcare Organizations (JCAHO).

In additional embodiments, comparing the cleaning program may include comparing cleaning within the facility with cleaning within at least one other facility.

BRIEF DESCRIPTION OF THE DRAWINGS

The foregoing features of the invention will be more readily understood by reference to the following detailed description, taken with reference to the accompanying drawings, in which:

FIG. 1 illustrates frequency of contamination of common hospital room locations by three pathogens.

FIGS. 10A and 10B illustrate detection of a transparent indicator material using a source of ultraviolet radiation.

DETAILED DESCRIPTION OF SPECIFIC EMBODIMENTS

Definitions. As used in this description and the accompanying claims, the following terms shall have the meanings indicated, unless the context otherwise requires:

Terminal cleaning refers to cleaning of a hospital room following departure of its most recent occupant and prior to the arrival of its immediately prospective occupant.

Black light refers to ultraviolet or UV radiation emanating from an ultraviolet source.

Transparent refers to capable of transmitting light so that objects and images beyond can be clearly perceived.

Nosocomial infections are infections arising from and transmitted within a hospital environment.

Cleaning of patient rooms is an ongoing process in a hospital. Each patient occupying a room may be subject to pathogens left by a prior occupant of the room and, in turn, may insert his or her specific pathogens into the room environment. An aim of room cleaning is to decrease the likelihood of the environmental transmission of infection to an occupant of the room. Some room sites are cleaned daily while others are cleaned following patient occupation. Generally, such cleaning is unsupervised. Correlation of the health of room occupants could provide an indication of the quality of the cleaning, although with significant effort and with significant delay.

Embodiments of the invention as discussed below illustrate where monitoring may provide timely assessment as to whether current cleaning activities are consistent with control over nosocomial infections and may have the potential for objectively evaluating cleaning and disinfecting activities in various health care settings. A nontoxic composition containing an indicator material which fluoresces with exposure to a black light is inconspicuous yet may be readily removed by housekeeping products. Small volumes of composition may be confidentially applied to target sites in patient rooms following terminal cleaning and the targets reevaluated following terminal cleaning after several patients have occupied the room.

In an example, evaluation of housekeeping practices at three hospitals have confirmed high rates of cleaning of traditional sites but poor cleaning of many sites which have significant potential for harboring and transmitting microbial pathogens. An integrated program may identify such deficiencies in hospital cleaning and target remediation efforts so as to accelerate reduction in pathogen levels.

Figure 2:
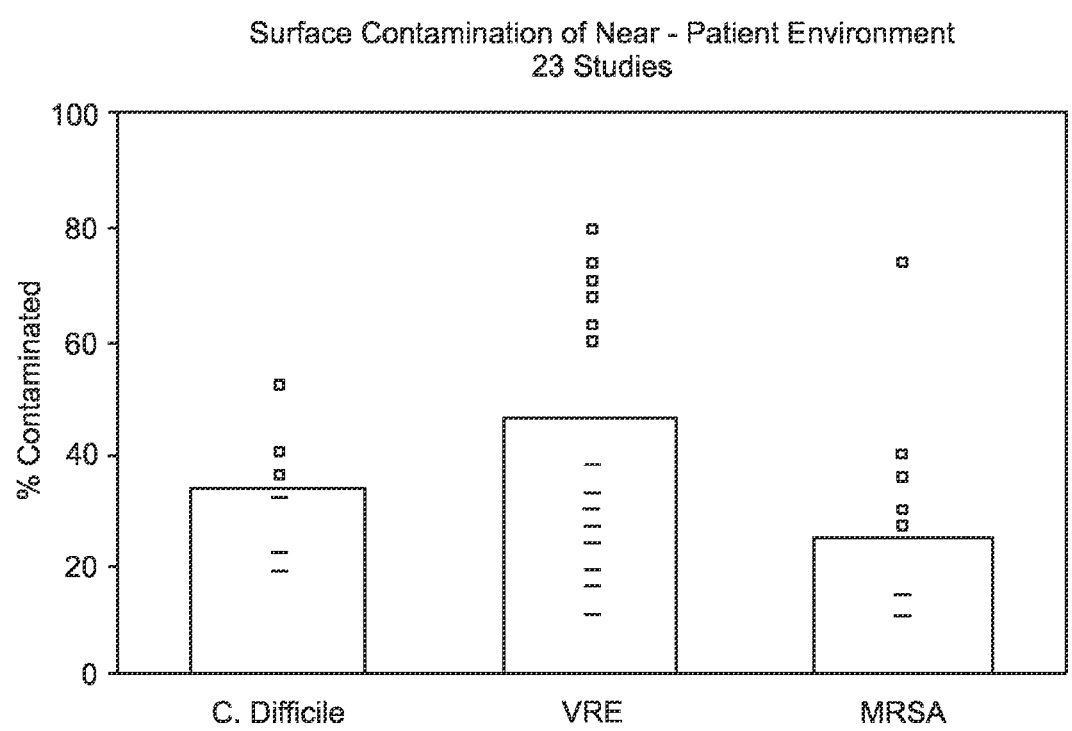
FIG. 2 illustrates the percentage of contamination of hospital surfaces by the pathogens of FIG. 1.
Figures 3, 4:
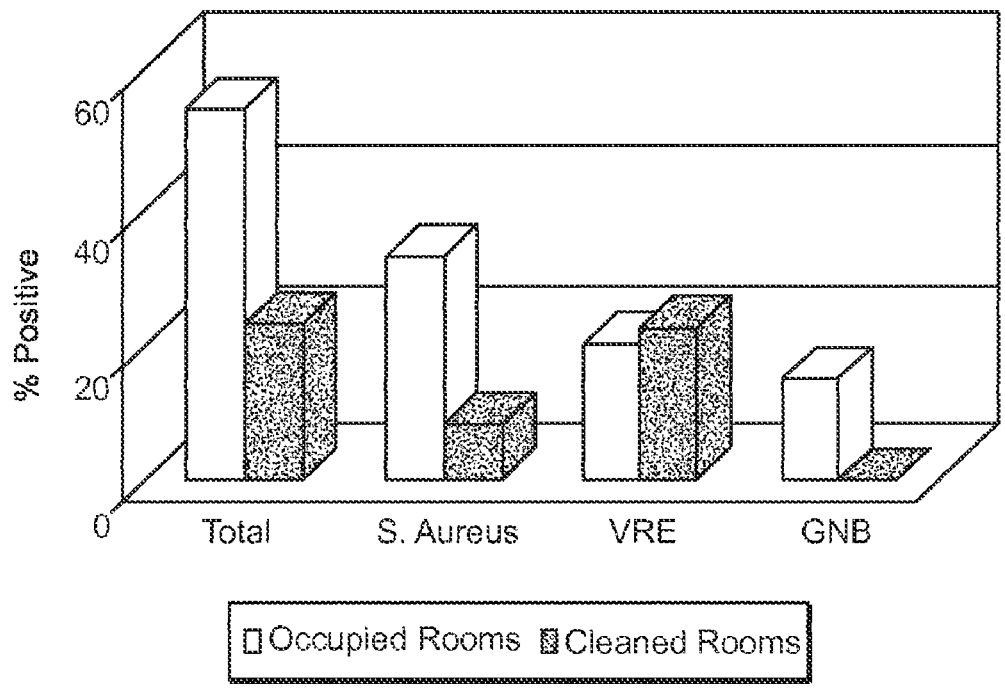
FIG. 3 illustrates survival of pathogens on inanimate surfaces.
FIG. 4 illustrates a microbiologic evaluation of patient room contamination and disinfection.
Figure 5:
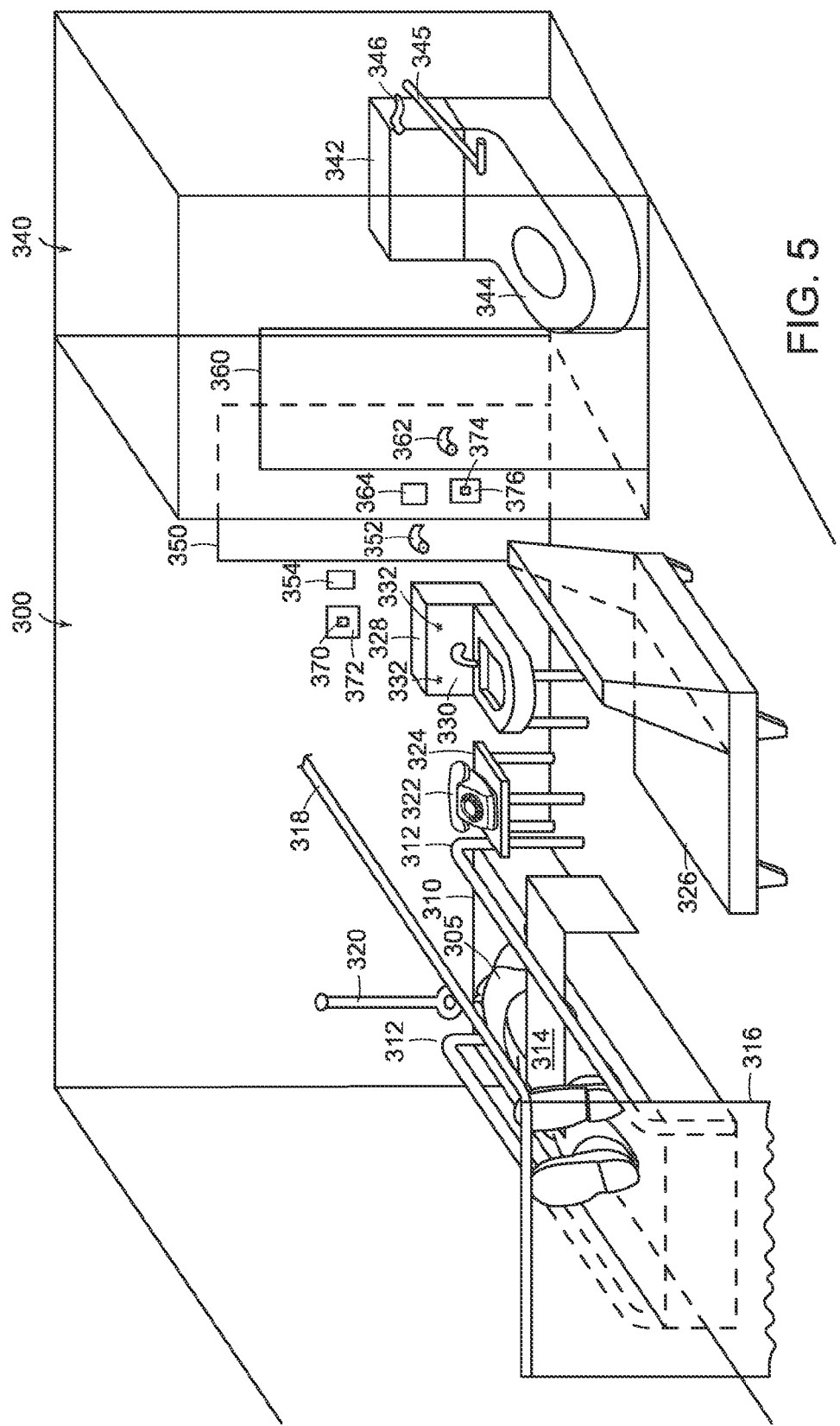
FIG. 5 illustrates the contents of a typical hospital room.

FIG. 5 illustrates a typical hospital room 300. Room 300 contains bed 310 in association with bed rails 312, bed tray 314, drape 316, and drape support 318. Patient call box 320 and telephone 322 are located proximal to bed 310 and provide communication, where telephone 322 rests on table 324. Chair 326 provides additional seating. Sink 328 including faucet 330, handles 332, and bedpan flushing device 334 provide a cleansing facility. Toilet 342 containing seat 344 and handle 346 resides in bathroom 340. Grab bar 348 provides support for patient 305 in using the toilet 342. Entry into room 300 and bathroom 340 is through doors 350 and 360 respectively via engagement of handle 352 or push plate 354 for door 350 and of handle 362 or push plate 364 for door 360. Room lights are adjusted by room light switch 370 mounted on room light switch plate 372. Bathroom lights are adjusted by bathroom light switch 374 mounted on bathroom light switch plate 376.

Figure 6:
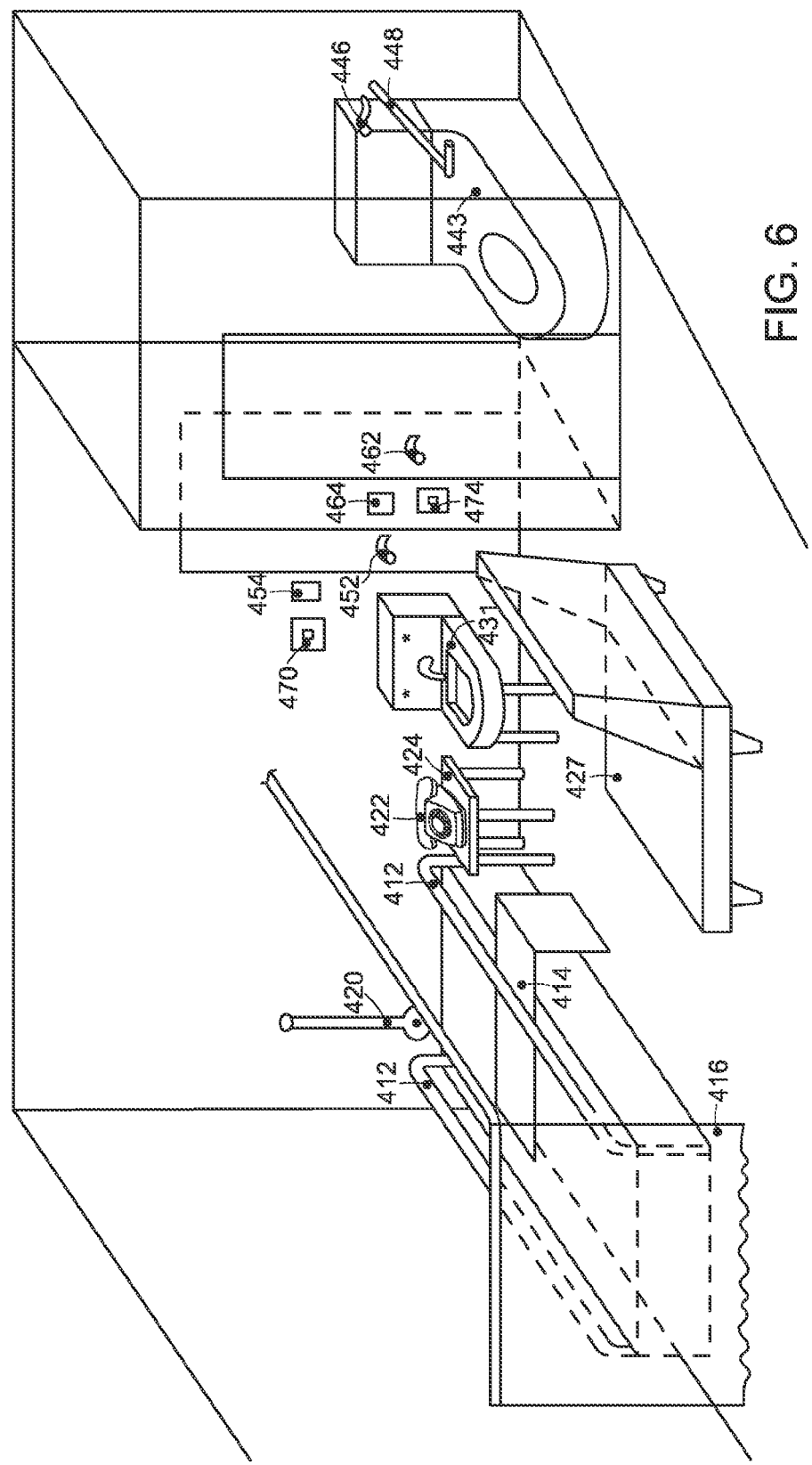
FIG. 6 illustrates typical locations of targets within a hospital room.

FIG. 6 illustrates targets for monitoring. These targets correspond to areas of a surface and may be chosen on the basis of the recommendation from the CDC that enhanced cleaning activities should be directed at "high touch" objects (HTOs), as well on reports in the literature of sites reported as being frequently contaminated with hospital associated pathogens. Such targets may include toilet handle target 446, horizontal surface target 443 of toilet bowl 342, bedpan flushing device target 434, horizontal surface target 431 of the sink 328 adjacent to the faucet 330, doorknob or door handle targets 452, 462 [or push/grab plate targets 454, 464], toilet area hand hold target 448 immediately adjacent to the toilet 342, bedside table target 424, telephone receiver target 422, call button target 420, overbed table target 414, seat target 427 of patient chair 326, bedrail target 412 adjacent to the head of the bed 310, drape target 416, room light switch target 470, and bathroom light switch target 474.

Figure 7:
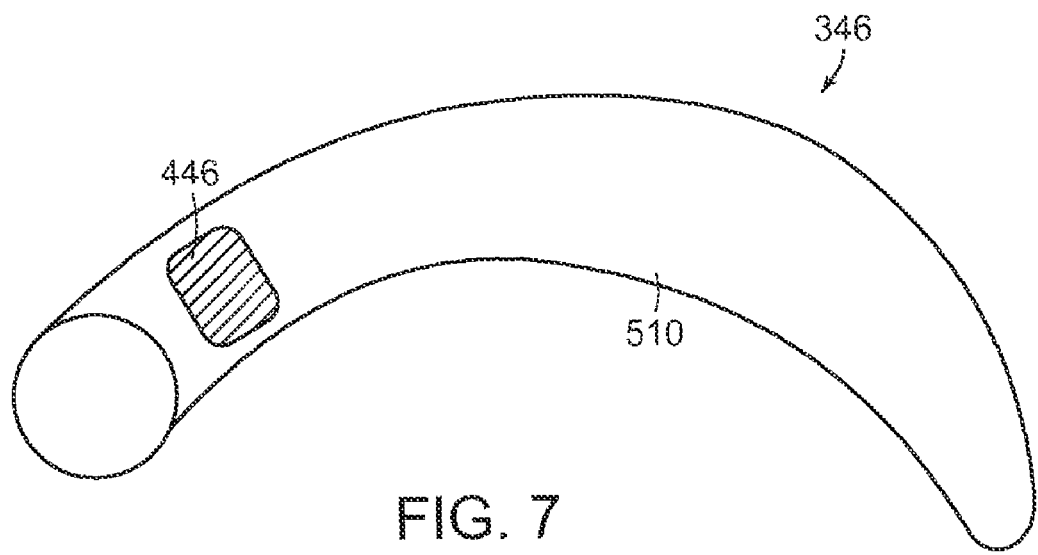
FIG. 7 illustrates a target located on a toilet handle.

To the degree possible, targets may be placed on the object to be monitored in an area which is easily accessible for cleaning and in close proximity to the portion of the object most frequently contaminated by patients' and health care workers' hands. As a consequence of this separation, indicator material placed on the targets is not subject to removal by the actions of the patient during the interval between placement of the indicator and the subsequent examination of the target. In addition, proximity of the targets to areas subject to patient contact makes probable that cleaning of the targets correlates with cleaning of the patient contact areas. For example, FIG. 7 illustrates location of toilet handle target 446 on toilet handle 346 that is separated from, but in the proximity of, region 510, the area most likely to receive patient contact during use and be contaminated.

Figure 8:
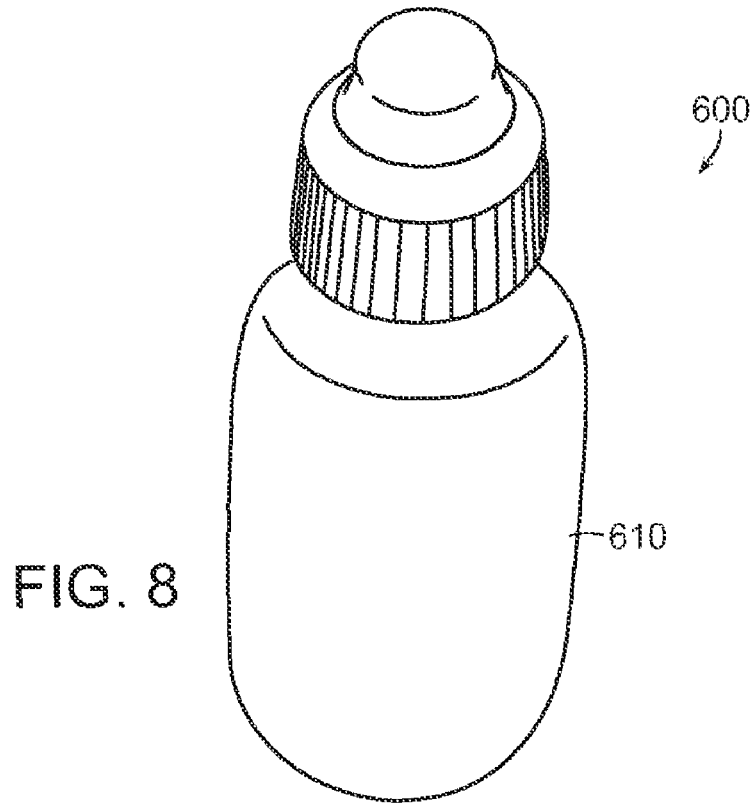
FIG. 8 illustrates a dispenser of a composition containing transparent indicator material.

FIG. 8 illustrates an applicator 600 for controllably applying a composition or targeting solution 610 for monitoring cleaning of a target such as toilet target 446. In FIG. 8, the applicator 600 is a plastic squeeze bottle. The composition 610 may be inconspicuous as by transparency, environmentally stable, and nontoxic, dry rapidly, be readily wetted by spray disinfectants, and be easily removed with light abrasion.

The composition 610 may include a carrier, a transparent indicator soluble in the carrier, a transparent source of adherence to the surface soluble in the carrier, and a surfactant. The carrier may be a biodegradable anionic or nonionic surfactant containing ammonium laureth sulfate, cocamide mea, cocamidopropyl betaine, ammonium laureth sulfate, sodium lauryl sulfate lauramide DEA, glycerine or sodium pareth-23 sulfate. The carrier may, in one embodiment, comprise between 35% and 55% percent of the composition. In one embodiment, the carrier may comprise 45% of the composition.

The transparent indicator may be a transparent ink such as Invisible Ink™ containing fluorescent blue/red water based tracer that is fluorescent under ultraviolet radiation. The transparent indicator, in one embodiment, may comprise between 3% and 5% of the composition. In one embodiment, the transparent ink may comprise 4% of the composition.

The transparent source of adherence may be a natural glue such as methyl cellulose or ethyl cellulose which may be available as powders. The source of adherence may, in one embodiment, comprised between 38% and 58% of the composition. In one embodiment, the source of adherence may comprise 48% of the composition.

The transparent surfactant may be polypropylene glycol with p-tert-octylphenoxy polyethoxyethyl alcohol (such as Photo-Flo™). In one embodiment, the transparent surfactant may comprise between 0.5% and 1.5% of the composition. In one embodiment, the transparent surfactant may comprise 1% of the composition.

Prior to cleaning of a room, the composition or targeting solution may be deposited on targets such as those indicated in FIG. 6 and fixed to the surface, as, for example, by being allowed to dry. Since the dried composition does not occupy a location likely to encounter abrasion from daily activities, its removal may be assumed to be the result of cleaning activities. When the dried targeting solution is transparent, those engaged in cleaning activities are unaware of target locations. Consequently, they are not biased to clean areas adjacent to the targets and to avoid non-adjacent areas.

Figure 9:
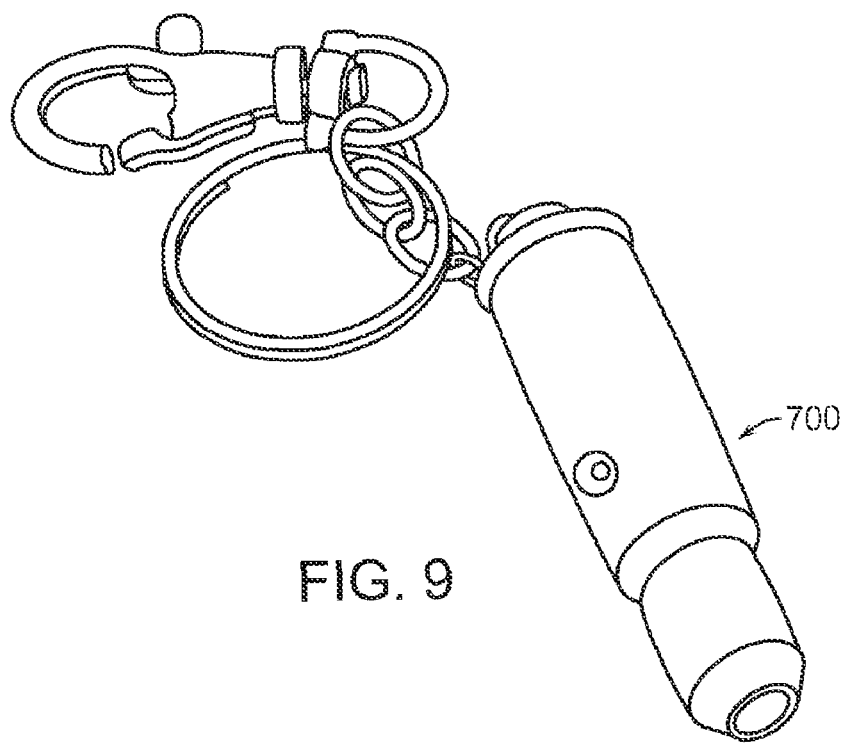
FIG. 9 illustrates a source of ultraviolet radiation.
Figure 10A:
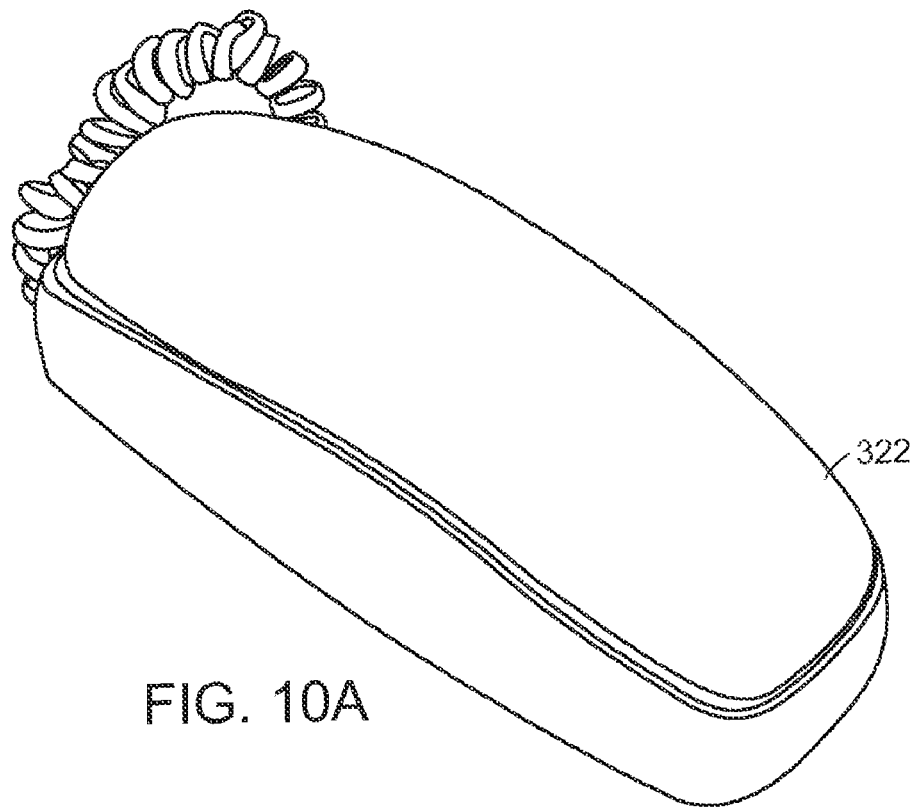

After a single cleaning opportunity or multiple cleaning opportunities are presented, cleaning activities may be suspended. That is, further cleaning in the room may not be permitted until the target areas are scanned. The targets within a room may be then scanned with a device able to render visible the dried composition so as to reveal the extent to which the targets have been subjected to cleaning. A target may be considered to have been cleaned if the dried composition was removed or clearly disturbed. If the composition contains a material fluorescent under exposure to ultraviolet radiation, a UV source 700 as shown in FIG. 9 may be held over the target locations to reveal dried composition not removed during cleaning. FIG. 10A shows the lack of visibility of a telephone receiver target 422 comprising fluorescent material on a telephone receiver 322 prior to cleaning under ordinary room illumination and FIG. 10B shows the visibility of the same target 422 under ultraviolet illumination from UV source 700, also prior to cleaning. If the transparent fluorescent material is Invisible Ink™ (Blacklight World), then an ultraviolet or UV source such as ULTRA9800 Ultra Mini Portable Black Light™ (Zigzagalightware) may permit observation of dried composition residues.

A study of hospital cleaning activities employing the above method, materials, and equipment has revealed deficiencies in cleaning.

Two of the hospitals involved in the study had similar demographics. They were both urban primary and secondary care institutions. Hospital A had 136 and hospital B had 115 medical/surgical beds with 15 and 14 bed combined medical/surgical intensive care units. Although the hospitals have geographic proximity, their administrative, clinical and housekeeping staffs are completely independent. Hospital C was a 60 bed acute care short-term rehabilitation hospital.

A targeting solution was used that contained an environmentally stable nontoxic base to which was added a chemical marker as a transparent indicator which fluoresced brightly when exposed to a black light, i.e. ultraviolet light. The targeting solution dried rapidly on surfaces to leave a residue that was inconspicuous, remained environmentally stable for several weeks, resisted dry abrasion, and was easily removed with moisture accompanied by minimal abrasion. Small plastic squeeze bottles were used to dispense approximately 0.2 ml. of solution to standardized target sites.

A group of 12 targets were chosen on the basis of the CDC's recommendation that enhanced cleaning activities should be directed at "high touch" surfaces [46], as well as sites reported in the previously cited literature as being frequently contaminated with hospital associated pathogens. Such surfaces included toilet handles, the horizontal surface of toilet bowls, bedpan flushing devices, horizontal surface of sinks adjacent to a faucet, doorknobs (or push/grab plates), toilet area hand holds immediately adjacent to the toilet, bedside tables, telephone receivers, call buttons, overbed tables, the seats of patient chairs and frequently contacted areas on bedrails. To the degree possible, the targeting material was placed on the high touch object (HTO) in an area which was easily accessible to cleaning and in close proximity to that portion of the object most frequently contacted by patients' and health care workers' hands.

HTOs were confidentially marked after a room had been terminally cleaned following discharge of its occupant. After two to three patients had occupied the room and the room was again terminally cleaned, a handheld black light was used to determine if the marked HTOs in the room had been cleaned. While the marking material was usually completely removed by routine disinfection cleaning, the object was considered cleaned if the target material was clearly disturbed. Patient room floors and room walls were not evaluated given the limited potential for their serving as a source of transmission of nosocomial pathogens [50]. Statistical data analysis was performed using a two tailed Fisher's exact test.

Figure 11:
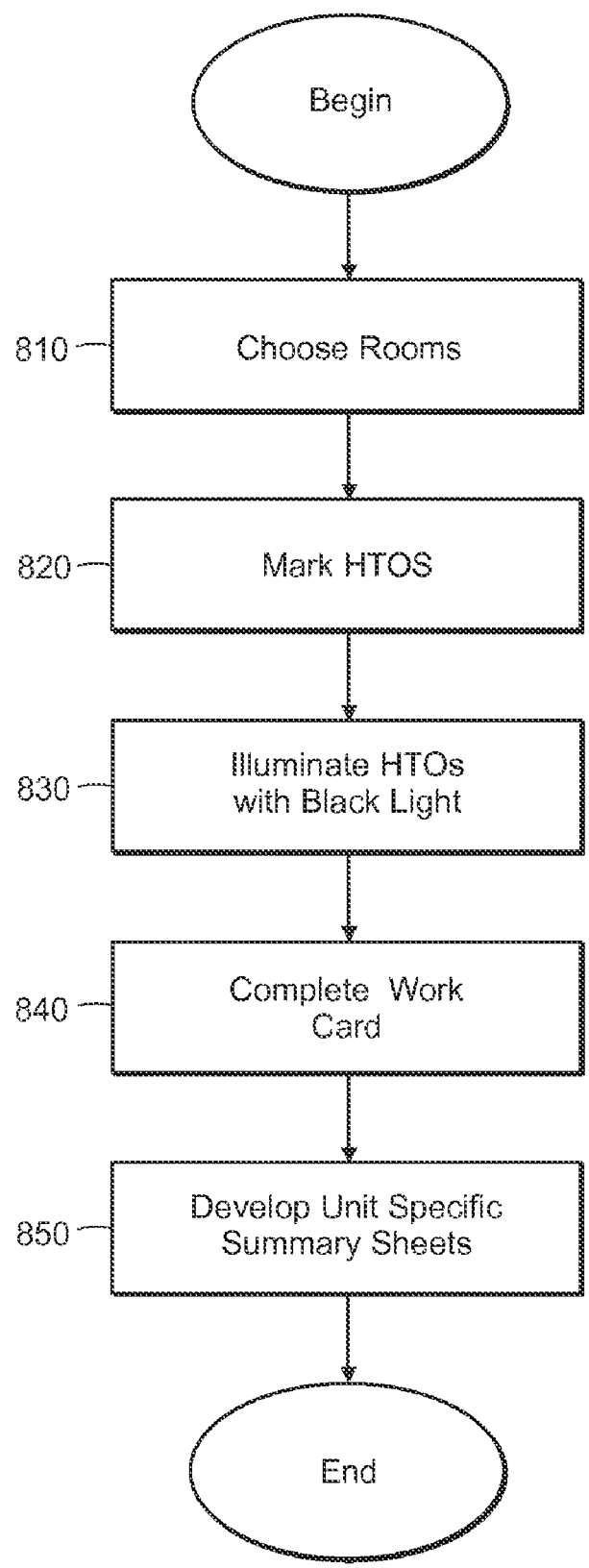
FIG. 11 illustrates a method for pre-intervention data collection.

FIG. 11 illustrates a method 800 for pre-intervention data collection. In step 810, rooms for evaluation are chosen randomly with representation from all medical/surgical (M/S) and intensive care (ICU) patient care units. In step 820, HTOs are confidentially marked after a room had been terminally cleaned following discharge of its occupant. At the time a target is marked, a standardized work card (supplied) is developed noting the date, room location and the HTOs marked. In step 830, after two to three patients have occupied the room and the room is again terminally cleaned on two or three occasions, a handheld black light is used to determine if the marked HTOs in the room have been cleaned. While the marking material is usually completely removed by routine disinfection cleaning, an object may be considered cleaned if the target material is clearly disturbed. In step 840, the work card is dated and completed on the basis of the observations made. In step 850, once between 50 and 60 rooms are evaluated, Unit Specific Summary Sheets (supplied) are developed to facilitate data analysis.

Figure 12:
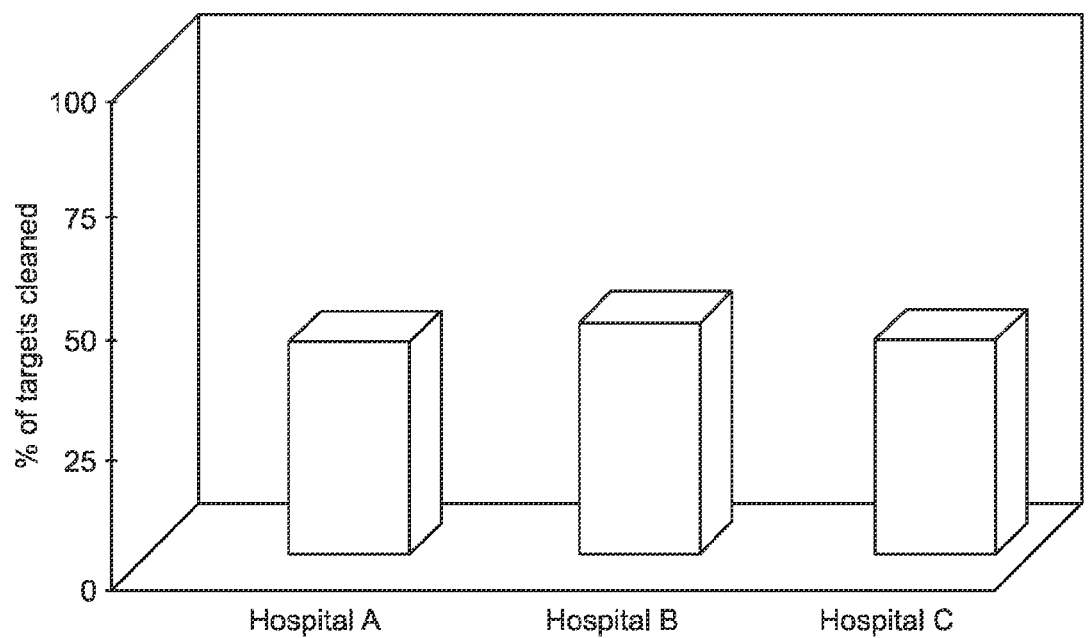
FIG. 12 illustrates results of monitoring the cleaning activities of three hospitals.
Figure 13:
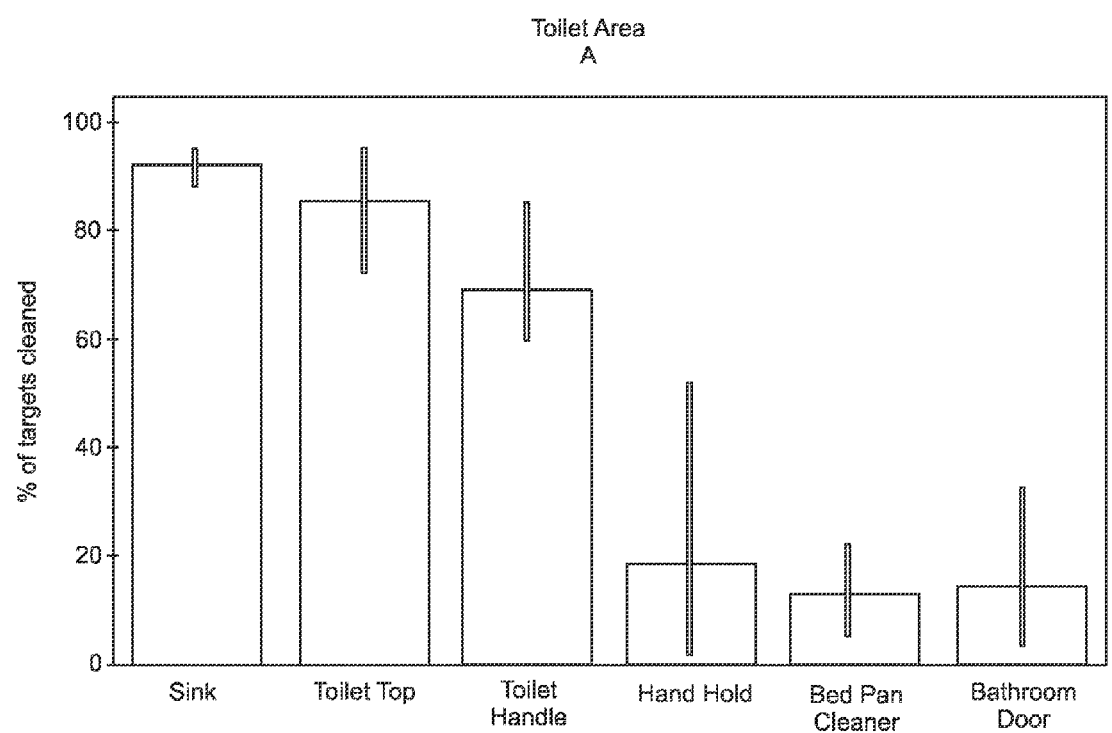
FIG. 13 illustrates results of monitoring of a toilet area of a hospital room.

During the study of periods ranging from one to four months, 60, 54 and 43 rooms were evaluated at the three hospitals respectively. Overall 47% of the 1404 HTOs evaluated were found to have been cleaned after several terminal cleanings. As illustrated in FIG. 12, similar rates of cleaning were found in each of the three hospitals. As illustrated in FIG. 13 for toilet areas and FIG. 14 for patient areas, high rates of cleaning, between 80% and 92%, were found for bedside tables, toilet tops, tray tables, and sinks. In contrast several HTOs, including bedpan cleaning equipment, patient room and bathroom doorknobs (or door pulls) as well as toilet handholds were cleaned in between 12.3% and 18% of rooms overall. The differences found between well cleaned objected (>80%) and poorly cleaned objects (<20%) in the three hospitals was highly significant (P=<0.001). The remaining objects, although more thoroughly cleaned than the group of poorly cleaned objects, were, as a group, still significantly less well cleaned than the objects cleaned greater than 80% of the time (mean=88.3% vs. 54.5%, P=<0.0001).

Although the CDC 2003 Guidelines for Environmental Infection Control in Healthcare Facilities recommends "cleaning and disinfection of high touch surfaces (e.g., doorknobs, bedrails, light switches in and around toilets in patients' rooms) on a more frequent schedule than minimal touch housekeeping services" (Environmental Services I, E, 3) [45], the aforementioned hospital results indicate that many of these HTOs were not cleaned as a regular part of terminal room cleaning. In view of the consistently high frequency of cleaning documented for sinks, toilet tops and tray tables, suboptimal cleaning of many HTOs such as bedpan cleaners, toilet area handholds and doorknobs may be the result of lack of appreciation for the potential role the latter objects have in the transmission of nosocomial pathogens rather than ineffective terminal disinfection cleaning in general.

Two of the least well cleaned HTOs, bedpan cleaners (mean 12.3%, range 9% to 20%) and toilet area handholds (mean 17.7%, range 0-50%), represent objects with a high potential for contamination by environmentally resilient gastrointestinal colonizing pathogens such as *C. difficile*, VRE and MRSA. In view of the effectiveness of disinfectants for a wide range of pathogens including antibiotic resistant bacteria, ineffectiveness of terminal cleaning/disinfection activities in substantially eliminating these pathogens from the near patient environment in other studies may be the result of suboptimal cleaning.

Figures 14, 15:
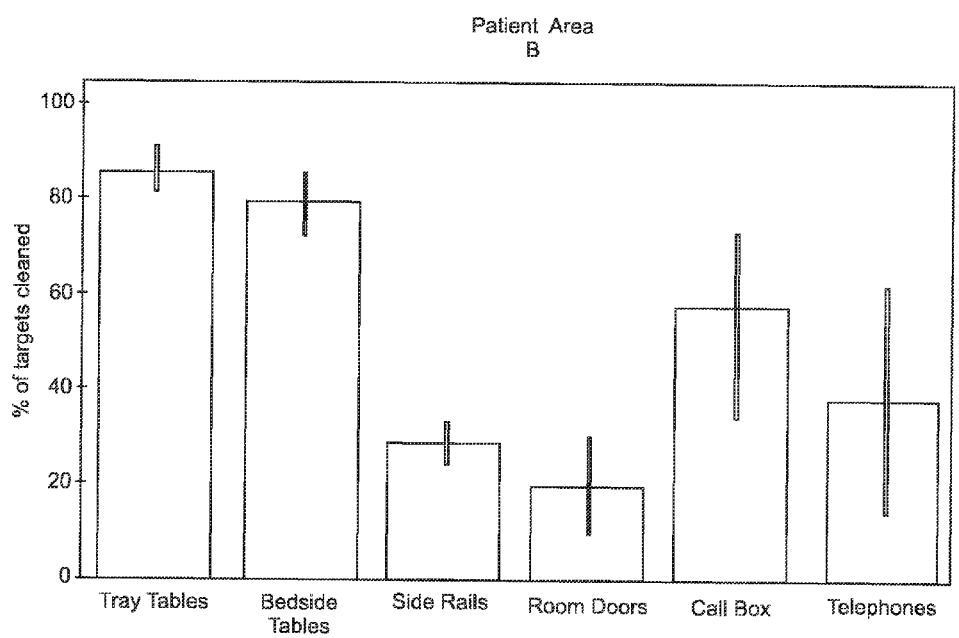
FIG. 14 illustrates results of monitoring of a patient area of a hospital room.
FIG. 15 illustrates a method for control of nosocomial pathogens.

FIG. 15 illustrates a method for control of nosocomial pathogens using the above technique as facilitated by an integrated program 1100 tailored to a particular health facility such as a hospital. The program involves sequential implementation of a baseline environmental evaluation system (BEES) 1120, a program enhancement system (PES) 1140, and a program comparison system (PCS) 1160. In the BEES 1120, Infection Control Practitioner (ICP) is provided and undertakes an assessment of the effectiveness of terminal cleaning in approximately 40 randomly chosen patient rooms. Members of the health care facility are made aware of the role of near patient environment in infection prevention and of the usefulness of transparent targets. During BEES 1120, site specific demographic data and pre-intervention data are collected and comparisons made within the health care facility or health care institution.

Once the pre-intervention status has been documented in BEES 1120, target monitoring activities are launched in PES 1140. Following an opportunity for administration leadership to comment on the baseline assessment phase, specific training is given to the general facility administration and to the environmental services staff before implementation of targeted cleaning and disinfection. Following evaluation of the initial intervention, structured graphic feedback on the results of the intervention is provided to administrative, environmental, and nursing services.

Next, in PCS 1160, the program is evaluated and feedback given on an ongoing basis, for example, every six months. Part of the feedback involves comparison of the health care facility to other institutions. Recognition may be tended to individuals within the program and to the program itself for favorable comparisons with outside institutions.

Although the above discussion disclosed various exemplary embodiments of the invention, it should be apparent that those skilled in the art can make various modifications that will achieve some of the advantages of the invention without departing from the true scope of the invention.

What is claimed is:

1. A method for improving cleaning of an environment comprising:
   (i) applying a transparent marker to one or more target sites located on one or more surfaces within an environment, the transparent marker capable of being viewed when exposed to ultraviolet (UV) radiation;
   (ii) determining if the transparent marker remains on the one or more target sites after one or more opportunities to clean the one or more surfaces by one or more environmental services staff members;
   (iii) establishing a quantitative baseline level of cleanliness for the one or more surfaces within the environment, the quantitative baseline level of cleanliness being based, at least in part, upon steps (i) and (ii);
   (iv) instructing the one or more environmental services staff members on cleanliness issues; and
   (v) evaluating whether the cleanliness of the environment has improved after instructing the one or more environmental services staff members by repeating steps (i) and (ii) to establish a post-instruction level of cleanliness and comparing the post-instruction level of cleanliness to the quantitative baseline level of cleanliness.

2. A method according to claim 1, wherein the one or more surfaces are high touch objects.

3. A method according to claim 1, wherein cleanliness issues include at least one selected from the group consisting of improved cleaning techniques, results of the quantitative baseline of cleanliness, locations of areas to be cleaned, and information relating to the transmission of pathogens.

4. A method according to claim 1, wherein the one or more surfaces within the environment are located in a single room.

5. A method according to claim 1, wherein the one or more surfaces within the environment are located in a plurality of rooms.

6. A method according to claim 1, further comprising:
   determining a percentage of cleaned surfaces based at least in part upon whether the transparent marker visibly remains, when exposed to UV radiation, on each of the one or more surfaces after being cleaned by one or more environmental services staff.

7. A method according to claim 1, further comprising categorizing the one or more surfaces as cleaned or not cleaned after the one or more opportunities to clean the one or more surfaces, wherein a surface is categorized as clean if the transparent marker is removed or disturbed.

8. The method according to claim 1, wherein a source of the UV radiation is a handheld device.

9. The method according to claim 1, wherein the quantitative baseline level of cleanliness and the post-instruction level of cleanliness are indications of the presence of pathogens on the one or more surfaces.

10. The method according to claim 9, wherein the pathogens include at least one selected from the group consisting of Methicillin Resistant *Staphylococcus aureus* (MRSA), *Clostridium difficile* (*C. difficile*), and vancomycin resistant *Enterococcus* (VRE).

11. The method according to claim 1, wherein the transparent marker resists dry abrasion.

12. The method according to claim 1, further comprising:
   performing continuous monitoring of the cleanliness of the environment by periodically repeating steps (i) and (ii) and establishing an updated level of cleanliness.

13. The method according to claim 1, wherein step (i) is performed prior to terminal cleaning of the environment and steps (ii)-(v) are performed after one or more terminal cleanings.

14. The method according to claim 1, further comprising:
   generating a list of the one or more target sites, the list including the location of the one or more target sites and when the transparent marker was applied to the one or more target sites.

15. A method according to claim 1 wherein the transparent marker resists dry abrasion.

16. A method according to claim 1, wherein the transparent marker, once applied, may only be removed using at least one of water and cleaning supplies.

17. The method according to claim 8, wherein the handheld device is a black light.

18. The method according to claim 17, wherein the handheld device is a directional UV flashlight.

19. The method according to claim 12 further comprising:
   re-instructing the one or more environmental services staff members on cleanliness issues and the updated level of cleanliness.

20. The method according to claim 14, wherein determining if the transparent marker remains on the one or more target sites includes using the list to determine the locations of the one or more target sites.

21. A method for improving cleaning procedures comprising:
   (i) applying an amount of transparent indicator material to one or more target sites located on one or more environmental surfaces within a first institution;
   (ii) determining if any of the transparent indicator material remains on the one or more target sites after one or more opportunities to clean the one or more environmental surfaces by one or more environmental services staff members;
   (iii) determining a pre-intervention level of cleanliness in the first institution, the pre-intervention level of cleanliness being a baseline and based, at least in part, upon whether transparent indicator material visibly remains, when exposed to UV radiation, on the one or more target sites;

(iv) altering existing cleaning procedures to enhance the first institution's cleaning and disinfecting program;

(v) determining a post-intervention level of cleanliness in the environment of the first institution by repeating steps (i) and (ii);

(vi) comparing the pre-intervention level of cleanliness to the post-intervention level of cleanliness to determine a change in cleanliness; and (vii) providing feedback regarding the change in cleanliness to the one or more environmental services staff members.

22. A method according to claim 21, further comprising comparing the pre-intervention and post-intervention levels of cleanliness with levels of cleanliness of a second institution.

23. A method according to claim 21, wherein determining the pre-intervention level of cleanliness includes collecting pre-intervention data and comparing the pre-intervention data to data collected from other units within the first institution.

24. A method according to claim 21, wherein altering existing cleaning procedures includes providing training to institutional administration and the one or more environmental services staff members.

25. A method according to claim 24, wherein training of institutional administration and the one or more environmental services staff members includes presenting the pre-intervention level of cleanliness.

26. A method according to claim 21 further comprising periodically re-evaluating the cleanliness of the first institution.

27. A method according to claim 21, wherein the transparent indicator material is resistant to dry abrasion.

28. The method according to claim 21, wherein step (i) is performed prior to terminal cleaning of the environment.

29. The method according to claim 21, further comprising:
generating a list of the one or more target sites, the list including the location of the one or more target sites and when the transparent marker was applied to the one or more target sites.

30. The method according to claim 29, wherein determining if the transparent marker remains on the one or more target sites includes using the list to determine the locations of the one or more target sites.

31. The method according to claim 21, wherein a source of the UV radiation is a directional UV flashlight.

32. A method according to claim 21, wherein the transparent indicator material, once applied, may only be removed using at least one of water and cleaning supplies.

33. A method for inspecting the cleanliness of an environment and training environmental services staff comprising:
pre-marking a plurality of high touch surfaces within an environment using an invisible indicator;
providing an opportunity for environmental services staff to clean the environment;
examining the pre-marked high touch surfaces using a source of UV radiation to determine whether the invisible indicator remains on the high touch surface after providing the opportunity for environmental services staff to clean the environment;
identifying high touch surfaces that require additional cleaning based at least in part on whether the invisible indicator remains on the high touch surface; and
providing training to the environmental services staff regarding cleaning of the environment.

34. A method according to claim 33, wherein providing training to the environmental services staff includes informing the environmental services staff about non-cleaned high touch surfaces.

35. A method according to claim 33, wherein the environmental services staff is unaware of the pre-marking of the plurality of high touch services.

36. A method according to claim 33, further comprising:
confirming that the plurality of high touch surfaces are sufficiently pre-marked prior to providing the opportunity to clean the environment.

37. A method according to claim 36, wherein confirming that the plurality of high touch surfaces are sufficiently pre-marked includes illuminating the pre-marked surface with a UV light.

38. A method according to claim 33, further comprising training the environmental services staff on proper cleaning techniques prior to pre-marking the surfaces.

39. A method according to claim 38, wherein providing training to the environmental services staff includes re-training on proper cleaning techniques.

40. A method according to claim 33, wherein the invisible indicator resists dry abrasion.

41. A method according to claim 33, wherein the invisible indicator may only be removed using at least one of water and cleaning supplies.

42. A method for controlling transmission of nosocomial pathogens within an environment of a facility comprising:
implementing a baseline environmental evaluation system to provide a pre-intervention level of cleanliness within the environment, the pre-intervention level of cleanliness being determined by applying an amount of transparent indicator material to one or more target sites located on one or more surfaces within an environment and determining if any of the transparent indicator material remains on the one or more target sites after one or more opportunities to clean the one or more surfaces by one or more environmental services staff members;
implementing a program enhancement system, the program enhancement system including training at least one of facility administration and the one or more environmental services staff members on the baseline level of cleanliness within the environment, and providing a post-intervention level of cleanliness; and
implementing a program comparison system, the program comparison system comparing the pre-intervention level of cleanliness with the post-intervention level of cleanliness.

43. A method according to claim 42, wherein implementing the program comparison system further includes re-evaluating the post-intervention level of cleanliness on an ongoing basis.

44. A method according to claim 42, wherein implementing the program comparison system further includes comparing the pre-intervention level of cleanliness and the post-intervention level of cleanliness of the environment within the facility with other facilities.

45. A method according to claim 42, wherein implementing the baseline environmental system includes determining site specific demographic data and pre-intervention data.

46. A method according to claim 42, wherein implementing the program enhancement system includes providing at least one of facility administration and the one or more environmental services staff members with feedback on the results of the training.

47. A method according to claim 42, wherein the post-intervention level of cleanliness is determined by applying a second amount of transparent indicator material to the one or more target sites located on the one or more surfaces within the environment and determining if any of the second amount of transparent indicator material remains on the one or more target site after a second one or more opportunities to clean the one or more surfaces by the one or more environmental services staff members.

48. A method according to claim 42, wherein the transparent indicator material resists dry abrasion.

49. A method according to claim 42, wherein the transparent indicator material, once applied, may only be removed using at least one of water and cleaning supplies.

* * * * *

(12) EX PARTE REEXAMINATION CERTIFICATE (8936th)
United States Patent
Carling

(10) Number: US 7,785,109 C1
(45) Certificate Issued: *Mar. 27, 2012

(54) MONITORING CLEANING OF SURFACES

(75) Inventor: Philip C. Carling, Hingham, MA (US)

(73) Assignee: Kleancheck Systems, LLC, Hingham, MA (US)

Reexamination Request:
No. 90/011,423, Jan. 10, 2011

Reexamination Certificate for:
Patent No.: 7,785,109
Issued: Aug. 31, 2010
Appl. No.: 12/483,884
Filed: Jun. 12, 2009

( * ) Notice: This patent is subject to a terminal disclaimer.

Related U.S. Application Data

(63) Continuation of application No. 11/335,905, filed on Jan. 19, 2007, now Pat. No. 7,718,395.
(60) Provisional application No. 60/666,391, filed on Mar. 30, 2005.

(51) Int. Cl.
*G09B 23/34* (2006.01)
*C12N 1/20* (2006.01)
*C12N 1/00* (2006.01)
*G01N 21/00* (2006.01)
*G06Q 10/00* (2006.01)
*G06Q 50/00* (2006.01)
*B60R 11/00* (2006.01)

(52) U.S. Cl. .................... 435/370; 250/459.1; 296/1.09; 296/24.34; 296/37.8; 297/188.16; 434/395; 435/252.1; 435/252.4; 435/252.7; 435/842; 435/882; 435/967; 705/7.39

(58) Field of Classification Search .................... 435/370
See application file for complete search history.

(56) References Cited

To view the complete listing of prior art documents cited during the proceeding for Reexamination Control Number 90/011,423, please refer to the USPTO's public Patent Application Information Retrieval (PAIR) system under the Display References tab.

*Primary Examiner* — Johnny F Railey, II

(57) ABSTRACT

A method for monitoring cleaning of a surface includes applying an amount of transparent indicator material to an area of a surface and measuring the amount of transparent indicator material remaining on the surface. The transparent indicator material may be fixed on the surface by drying and, when a fluorescent material, may be measured through exposure to ultraviolet radiation.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 15 is cancelled.

Claims 1, 3, 6, 9, 12, 19, 21-23, 25, 26, 33, 42-44 and 47 are determined to be patentable as amended.

Claims 2, 4, 5, 7, 8, 10, 11, 13, 14, 16-18, 20, 24, 27-32, 34-41, 45, 46, 48 and 49, dependent on an amended claim, are to be determined to be patentable.

New claims 50-61 are added and determined to be patentable.

1. A method for improving cleaning of an environment comprising:
   (i) applying a transparent marker to one or more target sites located on one or more surfaces within an environment, the transparent marker capable of being viewed when exposed to ultraviolet (UV) radiation, *wherein the transparent marker includes a transparent source of adherence and a surfactant*;
   (ii) determining if the transparent marker remains on the one or more target sites after one or more opportunities to clean the one or more surfaces by one or more environmental services staff members;
   (iii) establishing a quantitative baseline level of [cleanliness] *cleaning* for the one or more surfaces within the environment, the quantitative baseline level of [cleanliness] *cleaning* being based, at least in part, upon steps (i) and (ii) *and a rate of cleaning, wherein establishing the quantitative baseline level of cleaning includes determining a precentage of targets cleaned*;
   (iv) instructing the one or more environmental services staff members on [cleanliness] *cleaning* issues; and
   (v) evaluating whether the [cleanliness] *cleaning* of the environment has improved after instructing the one or more environmental services staff members by repeating steps (i) and (ii) to establish a post-instruction level of [cleanliness] *cleaning* and comparing the post-instruction level of [cleanliness] *cleaning* to the quantitative baseline level of [cleanliness] *cleaning, wherein establishing the post-instruction level of cleaning includes determining a percentage of targets cleaned after repeating steps (i) and (ii)*.

3. A method according to claim 1, wherein [cleanliness]*cleaning* issues include at least one selected from the group consisting of improved cleaning techniques, results of the quantitative baseline of [cleanliness] *cleaning*, locations of areas to be cleaned, and information relating to the transmission of pathogens.

6. A method according to claim 1, [further comprising:] *wherein* determining a percentage of *targets* cleaned [surfaces] *is* based at least in part upon whether the transparent marker visibly remains, when exposed to UV radiation, on each of the one or more surfaces after being cleaned by one or more environmental services staff.

9. The method according to claim 1, wherein the quantitative baseline level of [cleanliness] *cleaning* and the post-instruction level of [cleanliness] *cleaning* are indications of the presence of pathogens on the one or more surfaces.

12. The method according to claim 1, further comprising:
   performing continuous monitoring of the [cleanliness] *cleaning* of the environment by periodically repeating steps (i) and (ii) and establishing an updated level of [cleanliness] *cleaning*.

19. The method according to claim 12 further comprising:
   re-instructing the one or more environmental services staff members on [cleanliness] *cleaning* issues and the updated level of [cleanliness] *cleaning*.

21. A method for improving cleaning procedures comprising:
   (i) applying an amount of transparent indicator material to one or more target sites located on one or more environmental surfaces within a first institution, *wherein the transparent indicator material includes a transparent source of adherence and a surfactant*;
   (ii) determining if any of the transparent indicator material remains on the one or more target sites after one or more opportunities to clean the one or more environmental surfaces by one or more environmental services staff members;
   (iii) determining a pre-intervention level of [cleanliness] *cleaning* in the first institution, the pre-intervention level of [cleanliness] *cleaning* being a baseline and based, at least in part, upon whether transparent indicator material visibly remains, when exposed to UV radiation, on the one or more target sites *and a rate of cleaning, wherein determining the pre-intervention level of cleaning includes determining a percentage of targets cleaned*;
   (iv) altering existing cleaning procedures to enhance the first institution's cleaning and disinfecting program;
   (v) determining a post-intervention level of [cleanliness] *cleaning* in the environment of the first institution by repeating steps (i) and (ii), *wherein determining the post-intervention level of cleaning includes determining a percentage of targets cleaned after repeating steps (i) and (ii)*;
   (vi) comparing the pre-intervention level of [cleanliness] *cleaning* to the post-intervention level of [cleanliness] *cleaning* to determine a change in [cleanliness] *cleaning*; and
   (vii) providing feedback regarding the change in [cleanliness] *cleaning* to the one or more environmental staff members.

22. A method according to claim 21, further comprising comparing the pre-intervention and post-intervention levels of [cleanliness] *cleaning* with levels of [cleanliness ] *cleaning* of a second institution.

23. A method according to claim 21, wherein determining the pre-intervention level of [cleanliness] *cleaning* includes collecting pre-intervention data and comparing the pre-intervention data to data collected from other units within the first institution.

25. A method according to claim 24, wherein training of institutional administration and the one or more environmental services staff members includes presenting the pre-intervention level of [cleanliness] *cleaning*.

26. A method according to claim 21 further comprising periodically re-evaluating the [cleanliness] *cleaning* of the first institution.

33. A method for inspecting the [cleanliness] *cleaning* of an environment and training environmental services staff comprising:
- pre-marking a plurality of high touch surfaces within an environment using an invisible indicator, *the invisible indicator including a transparent source of adherence and a surfactant*;
- providing an opportunity for environmental services staff to clean the environment;
- examining the pre-marked high touch surfaces using a source of UV radiation to determine whether the invisible indicator remains on the high touch surface after providing the opportunity for environmental services staff to clean the environment;
- identifying high touch surfaces that require additional cleaning based at least in part on whether the invisible indicator remains on the high touch surface; and
- providing training to the environmental services staff regarding cleaning of the environment.

42. A method for controlling transmission of nosocomial pathogens within an environment of a facilitiy comprising:
- implementing a baseline environmental evaluation system to provide a pre-intervention level of [cleanliness] *cleaning* within the environment, the pre-intervention level of [cleanliness] *cleaning* being determined by applying an amount of transparent indicator material to one or more target sites located on one or more surfaces within an environment and determining if any of the transparent indicator material remains on the one or more target sites after one or more opportunities to clean the one or more surfaces by one or more environmental services staff member, *the pre-intervention level of cleaning being based, at least in part, on a rate of cleaning and includes determining a percentage of targets cleaned, the transparent indicator material including a transparent source of adherence and a surfactant*;
- implementing a program enhancement system, the program enhancement system including training at least one of facility administration and the one or more environmental services staff members on the baseline level of [cleanliness] *cleaning* within the environment, and providing a post-intervention level of [cleanliness] *cleaning*; and
- implementing a program comparison system, the program comparison system comparing the pre-intervention level of [cleanliness] *cleaning* with the post-intervention level of [cleanliness] *cleaning*.

43. A method according to claim 42, wherein implementing the program comparison system further includes re-evaluating the post-intervention level of [cleanliness] *cleaning* on an ongoing basis.

44. A method according to claim 42, wherein implementing the program comparison system further includes comparing the pre-intervention level of [cleanliness] *cleaning* and the post-intervention level of [cleanliness] *cleaning* of the environment within the facility with other facilities.

47. A method according to claim 42, wherein the post-intervention level of [cleanliness] *cleaning* is determined by applying a second amount of transparent indicator material to the one or more target sites located on the one or more surfaces within the environment and determining if any of the second amount of transparent indicator material remains on the one or more target site after a second one or more opportunities to clean the one or more surfaces by the one or more environmental services staff members, *wherein the post-intervention level of cleaning is based, at least in part, on a rate of cleaning and includes determining a percentage of targets cleaned.*

*50. A method according to claim 1, wherein the rate of cleaning is based upon the percentage of targets cleaned.*

*51. A method according to claim 1, wherein the percentage of targets cleaning includes at least one of the percentage of sites in which the transparent marker is completely removed, and the percentage of sites in which the transparent marker is clearly disturbed.*

*52. A method according to claim 1, wherein post-instruction level of cleaning is based, at least in part, upon repeated steps (i) and (ii) and a post instruction rate of cleaning.*

*53. A method according to claim 1, wherein establishing the post-instruction level of cleaning includes determine a post-instruction percentage of targets cleaned.*

*54. A method according to claim 53, wherein the post-instruction rate of cleaning is based upon the post-instruction percentage of targets cleaned.*

*55. A method according to claim 53, wherein the post-instruction percentage of targets cleaning includes at least one of the percentage of sites in which the transparent marker is completely removed, and the percentage of sites in which the transparent marker is clearly disturbed.*

*56. A method according to claim 1, wherein the transparent source of adherence is a natural glue.*

*57. A method according to claim 1, wherein the transparent marker also includes a transparent indicator, the percentage of transparent source of adherence within the transparent marker is substantially greater than the percentage of transparent indicator within the transparent marker.*

*58. A method according to claim 1, wherein the transparent marker includes between 38% and 58% transparent source of adherence.*

*59. A method according to claim 21, wherein the transparent source of adherence is a natural glue.*

*60. A method according to claim 33, wherein the transparent source of adherence is a natural glue.*

*61. A method according to claim 42, wherein the transparent source of adherence is a natural glue.*

* * * * *